United States Patent
Ko et al.

(10) Patent No.: US 12,239,422 B2
(45) Date of Patent: Mar. 4, 2025

(54) APPARATUS FOR ESTIMATING BIOLOGICAL-INFORMATION AND SENSOR FOR MEASURING MULTI-SIGNAL

(71) Applicant: SAMSUNG ELECTRONICS CO., LTD., Suwon-si (KR)

(72) Inventors: Byung Hoon Ko, Hwaseong-si (KR); Yong Joo Kwon, Yongin-si (KR); Seung Woo Noh, Seongnam-si (KR); Hyun Seok Moon, Hwaseong-si (KR); Sung Mo Ahn, Yongin-si (KR); Kun Sun Eom, Yongin-si (KR); Jong Wook Lee, Suwon-si (KR); Tak Hyung Lee, Seoul (KR); Myoung Hoon Jung, Bucheon-si (KR); Chang Mok Choi, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 932 days.

(21) Appl. No.: 17/349,419

(22) Filed: Jun. 16, 2021

(65) Prior Publication Data

US 2022/0125321 A1   Apr. 28, 2022

(30) Foreign Application Priority Data

Oct. 22, 2020  (KR) .................. 10-2020-0137683
Mar. 15, 2021  (KR) .................. 10-2021-0033535

(51) Int. Cl.
*A61B 5/0205*   (2006.01)
*A61B 5/00*   (2006.01)
(Continued)

(52) U.S. Cl.
CPC ........ *A61B 5/0205* (2013.01); *A61B 5/14552* (2013.01); *A61B 5/681* (2013.01);
(Continued)

(58) Field of Classification Search
CPC ... A61B 5/1455; A61B 5/14552; A61B 5/681; A61B 5/6885; A61B 5/7221; A61B 5/742
See application file for complete search history.

(56) References Cited

U.S. PATENT DOCUMENTS 7,697,966 B2 *  4/2010  Monfre ............... A61B 5/1455
                                                         600/316
10,156,867 B2   12/2018  von Badinski et al.
(Continued)

FOREIGN PATENT DOCUMENTS

KR   10-2016-0090125 A   7/2016
KR   10-2017-0004607 A   1/2017
(Continued)

OTHER PUBLICATIONS

Communication issued Apr. 18, 2023 by the Korean Intellectual Property Office in counterpart to Korean Patent Application No. 10-2021-0033535.
(Continued)

*Primary Examiner* — Eric F Winakur
(74) *Attorney, Agent, or Firm* — Sughrue Mion, PLLC

(57) ABSTRACT

An apparatus for estimating biological information may include a sensor configured to detect a first light signal and a second light signal from an object of a user and a processor configured to determine whether a condition for estimating biological information is satisfied based on the detected first light signal and estimate biological information based on the second light signal, wherein the sensor includes a force sensor configured to measure a force applied to the object when the object is in contact with a cover surface of the sensor.

14 Claims, 14 Drawing Sheets

(51) Int. Cl.
*A61B 5/1455* (2006.01)
*A61B 90/00* (2016.01)

(52) U.S. Cl.
CPC .......... *A61B 5/6885* (2013.01); *A61B 5/7221* (2013.01); *A61B 5/742* (2013.01); *A61B 90/06* (2016.02); *A61B 2090/064* (2016.02)

(56) References Cited

U.S. PATENT DOCUMENTS

| | | | |
|---|---|---|---|
| 10,420,470 | B2 | 9/2019 | Kwon et al. |
| 10,448,848 | B2 | 10/2019 | Park et al. |
| 10,694,997 | B2 | 6/2020 | Kim et al. |
| 10,772,505 | B2 | 9/2020 | Kim |
| 11,000,192 | B2 | 5/2021 | Kang et al. |
| 2002/0169381 | A1 | 11/2002 | Asada et al. |
| 2016/0238443 | A1 | 8/2016 | Chu et al. |
| 2019/0076032 | A1 | 3/2019 | Park et al. |
| 2019/0313979 | A1 | 10/2019 | Kang et al. |
| 2019/0365231 | A1 | 12/2019 | Kwon et al. |
| 2020/0000353 | A1 | 1/2020 | Park et al. |
| 2020/0146569 | A1 | 5/2020 | Lee et al. |
| 2020/0229743 | A1 | 7/2020 | Choi et al. |
| 2020/0245880 | A1 | 8/2020 | Choi et al. |
| 2020/0253561 | A1 | 8/2020 | Han et al. |
| 2020/0297223 | A1 | 9/2020 | Cho |

FOREIGN PATENT DOCUMENTS

| | | |
|---|---|---|
| KR | 10-2017-0041117 A | 4/2017 |
| KR | 10-2019-0007634 A | 1/2019 |
| KR | 10-2019-0048873 A | 5/2019 |
| KR | 10-2019-0056871 A | 5/2019 |
| KR | 10-2020-0020341 A | 2/2020 |
| KR | 10-2020-0091625 A | 7/2020 |
| KR | 10-2020-0095891 A | 8/2020 |
| KR | 10-2020-0112095 A | 10/2020 |
| WO | 2019069814 A1 | 4/2019 |
| WO | 2020183497 A1 | 9/2020 |

OTHER PUBLICATIONS

Communication dated Jan. 21, 2022 issued by the European Patent Office in counterpart European Application No. 21187666.9.

* cited by examiner

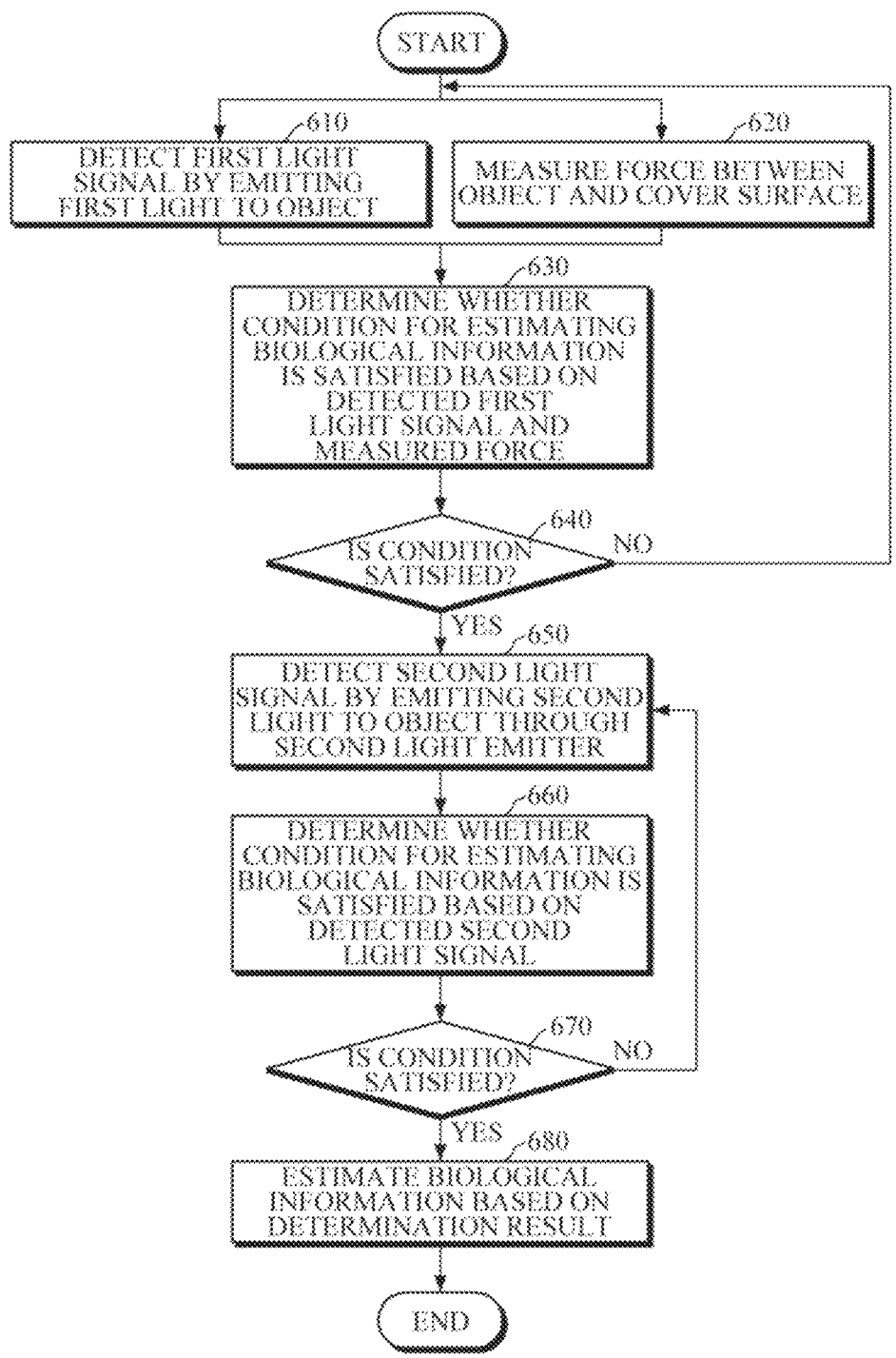

APPARATUS FOR ESTIMATING BIOLOGICAL-INFORMATION AND SENSOR FOR MEASURING MULTI-SIGNAL

CROSS-REFERENCE TO RELATED APPLICATION(S)

This application claims priority from Korean Patent Application No. 10-2020-0137683, filled on Oct. 22, 2020, and Korean Patent Application No. 10-2021-0033535, filed on Mar. 15, 2021, in the Korean Intellectual Property Office, the disclosures of which are incorporated herein by reference in their entireties.

BACKGROUND

1. Field

Apparatuses and methods consistent with example embodiments relate to estimating biological information and a sensor for measuring a multi-signal for estimating biological information.

2. Description of Related Art

As medical science has progressed and average life expectancy has increased, an interest in health care has increased. Also, interest in medical equipment/devices has increased to extend from middle-sized or small-sized medical devices and health-care devices that may be kept at home or carried by individuals, to large-sized medical devices that can be utilized by hospitals and inspection agencies. Medical devices for measuring biological information may include invasive devices and non-invasive devices. Using a non-invasive device, biological information may be detected in a relatively simple manner without causing pain to a subject, but the accuracy of the measurement result is low, and thus various studies have been conducted to overcome such a drawback.

SUMMARY

According to an aspect of an example embodiment, there is provided an apparatus for estimating biological information, including: a sensor configured to detect a first light signal and a second light signal that are reflected or scattered from a body part of a user; and a processor configured to determine whether a condition for estimating the biological information is satisfied based on the first light signal, and in response to the biological information being satisfied, estimate the biological information based on the second light signal, wherein the sensor may include: a cover surface configured to be in contact with the body part; a first light emitter disposed on a first substrate and configured to emit a first light to the body part; a second light emitter disposed on a second substrate and configured to emit a second light, the second substrate being disposed closer to the cover surface than to the first substrate; a light detector configured to detect the first light signal from the first light that is emitted to and then scattered or reflected from the body part, and detect the second light signal from the second light that is emitted to and then scattered or reflected from the body part; and a force sensor configured to measure a force applied to the body part when the body part is in contact with the cover surface.

The processor may be further configured to obtain a contact image of the body part based on the first light signal, determine a contact state of the body part based on at least one of the contact image or the force measured by the force sensor, and determine whether the condition for estimating biological information is satisfied based on the determined contact state.

Based on the condition being determined to be not satisfied, the processor may be further configured to guide the user to adjust the contact state.

The processor may be further configured to drive the first light emitter when the body part is in contact with the cover surface, and turn off the first light emitter and turn on the second light emitter when the contact state meets a condition for biological information estimation.

When the second light signal is received by the light detector, the processor may be further configured to determine whether the condition for estimating the biological information is satisfied based on a signal to noise ratio (SNR) of the received second light signal.

Based on the condition being determined to be not satisfied, the processor may be further configured to drive the second light emitter to re-obtain the second light signal.

When the body part is in contact with the cover surface and the force is measured by the force sensor, the processor may be further configured to determine a type of the biological information to be estimated based on the measured force.

The processor may be further configured to control at least one of a wavelength, current intensity, or duration of the second light emitter according to a driving condition of the second light emitter corresponding to the determined type of the biological information.

The apparatus may further include a display configured to display a first graphical object representing a reference force for each of a plurality of different types of biological information and a second graphical object representing the force measured by the force sensor.

The processor may be further configured to provide a list of a plurality of different types of biological information to the user and control the second light emitter according to a driving condition of the second light emitter corresponding to a biological information type selected by the user from the list.

The apparatus may further include a display configured to display a first graphical object representing the plurality of different types of biological information and a second graphical object representing a reference force for the selected biological information type.

The biological information may be at least one of heart rate, oxygen saturation, respiration rate, triglyceride, blood pressure, or antioxidant index.

According to an aspect of another example embodiment, there is provided an apparatus for estimating biological information, including: a sensor configured to detect a first light signal and a second light signal that are reflected or scattered from a body part of a user; and a processor configured to determine whether a condition for estimating the biological information is satisfied based on the first light signal, and in response to the biological information being satisfied, estimate the biological information based on the second light signal, wherein the sensor may include: a cover surface configured to be in contact with the body part; a first light emitter disposed on a first surface of a substrate and configured to emit first light to a reflector; a second light emitter disposed on a second surface of the substrate and configured to emit second light to the body part; the reflector disposed in a direction opposite to the cover surface with respect to the substrate and configured to reflect the first light emitted from the first light emitter toward the body part; a light detector configured to detect the first light signal from the first light that is emitted to and then scattered or reflected from the body part, and detect the second light signal from the second light that is emitted to and then scattered or reflected from the body part; and a force sensor configured to measure a force applied to the body part when the body part is in contact with the cover surface.

The apparatus may further include a partition wall configured to block the first light emitted from the first light emitter from traveling directly to the light detector.

The processor may be further configured to obtain a contact image of the body part based on the first light signal, determine a contact state of the body part based on at least one of the contact image or the force measured by the force sensor, and determine whether the condition for estimating the biological information is satisfied based on the determined contact state.

Based on the condition being determined to be is not satisfied, the processor may be further configured to guide the user to adjust the contact state.

When the second light signal is received by the light detector, the processor may be further configured to determine whether the condition for estimating the biological information is satisfied based on a signal to noise ratio (SNR) of the received second light signal.

Based on the condition being determined to be not satisfied, the processor may be further configured to drive the second light emitter to re-obtain the second light signal.

When the body part is in contact with the cover surface and the force is measured by the force sensor, the processor may be further configured to determine a type of the biological information to be estimated based on the measured force.

According to an aspect of another example embodiment, there is provided a sensor for measuring a multi-signal, the sensor including: a cover surface configured to be in contact with an object; a first light emitter disposed on a first substrate and configured to emit first light to the object; a second light emitter disposed on a second substrate and configured to emit second light to the object; the second substrate being disposed closer to the cover surface than to the first substrate; a light detector configured to detect a first light signal from the first light that is emitted to and then scattered or reflected from the object, and detect a second light signal from the second light that is emitted to and then scattered or reflected from the object based on the second light; and a force sensor configured to measure a force applied to the object when the object is in contact with the cover surface.

The first light and the second light have different wavelengths.

The sensor may further include a condenser configured to condense the first light and the second light scattered or reflected from the object in a direction toward the light detector.

The second substrate may include a transmissive region at a center of the second substrate to guide the first light and the second light scattered or reflected from the object to be directed toward the light detector, and the second light emitter may include a plurality of light sources arranged along an outer periphery of the transmissive region.

According to an aspect of another example embodiment, there is provided a sensor for measuring a multi-signal, the sensor including: a cover surface configured to be in contact with an object; a first light emitter disposed on a first surface of a substrate and configured to emit first light to a reflector; a second light emitter disposed on a second surface of the substrate and configured to emit second light to the object; the reflector disposed in a direction opposite to the cover surface with respect to the substrate and configured to reflect the first light emitted from the first light emitter toward the object; a light detector configured to detect a first light signal from the first light that is emitted to and then scattered or reflected from the object, and detect a second light signal from the second light that is emitted to and then scattered or reflected from the object; and a force sensor configured to measure a force applied to the object when the object is in contact with the cover surface.

The sensor may further include a partition wall configured to block the first light emitted from the first light emitter from traveling directly to the light detector.

According to an aspect of another example embodiment, there is provided an apparatus for estimating bio-information, the apparatus including: an optical sensor configured to detect an optical signal from light that is emitted to and then reflected or scattered from an object; a memory storing a plurality of different target forces corresponding to a plurality of different bio-information types, respectively; a force sensor configured to measure an external force exerted onto the apparatus; and a processor configured to: identify a bio-information type that is selected from the plurality of different bio-information types, provide a guidance of adjusting the external force to a target force corresponding to the identified bio-information type, among the plurality of different target forces; and based on the external force corresponding to the target force, estimate the bio-information having the identified bio-information type, based on the optical signal.

BRIEF DESCRIPTION OF THE DRAWINGS

The above and/or other aspects will be more apparent by describing certain example embodiments, with reference to the accompanying drawings, in which:

FIG. 6 is a flowchart illustrating a method of estimating biological information according to an exemplary embodiment;

DETAILED DESCRIPTION

Figure 1:
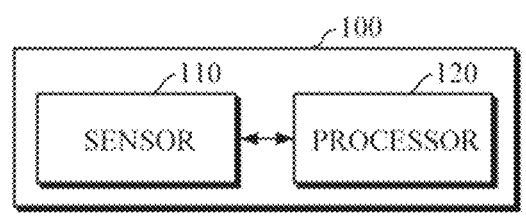
FIG. 1 is a block diagram illustrating an apparatus for estimating biological information according to an exemplary embodiment.

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

While such terms as "first," "second," etc., may be used to describe various elements, such elements must not be limited to the above terms. The above terms may be used only to distinguish one element from another.

FIG. 1 is a block diagram illustrating an apparatus for estimating biological information according to an exemplary embodiment. Referring to FIG. 1, an apparatus 100 for estimating biological information includes a sensor 110 and a processor 120.

The sensor 110 may detect a first light signal and a second light signal from an object of a user. In particular, the object may be a part of a human body, for example, a distal body portion, such as a finger, a toe, or the like, which has a high density of blood vessels, or a region of a wrist adjacent to the radial artery or an upper area of the wrist through which capillary blood or venous blood passes. The sensor 110 may include an optical sensor and a force sensor. The optical sensor may include a first light emitter configured to emit first light to the object and a second light emitter configured to emit second light to the object. The first light emitter and the second light emitter may include at least one of one or more light emitting diodes (LEDs), laser diodes, or phosphors, but are not limited thereto. The first light emitted by the first light emitter and the second light emitted by the second light emitter may have different wavelengths.

In addition, the optical sensor may further include a light detector configured to detect light scattered or reflected from the object. The light detector may detect a first light signal when the first light emitted from the first light emitter is scattered or reflected from the object, and also detect a second light signal when the second light emitted from the second light emitter is scattered or reflected from the object. The light detector may include a photodiode, a photo transistor (PTr), an image sensor, for example, a complementary metal-oxide semiconductor (CMOS) image sensor or a charge-coupled device (CCD) image sensor.

The a force sensor may measure a force applied to the object when the object is in contact with a cover surface. In order to induce a change in the amplitude of a pulse wave, the force sensor may measure the force applied to the object when the user gradually increases or decreases a pressing force while the finger is in contact with the cover surface of the sensor. For example, the force sensor may include a strain gauge, but is not limited thereto. In addition, the force sensor may be formed as a force sensor array. The sensor 110 may further include an area sensor, and may obtain a contact pressure based on a force and a contact area obtained through the force sensor and the area sensor.

FIGS. 3A to 4B are diagrams for explaining a structure of a sensor according to an exemplary embodiment. The structure of the sensor 110 shown in FIG. 1 will be described with reference to FIGS. 3A to 4B.

Figure 3A:
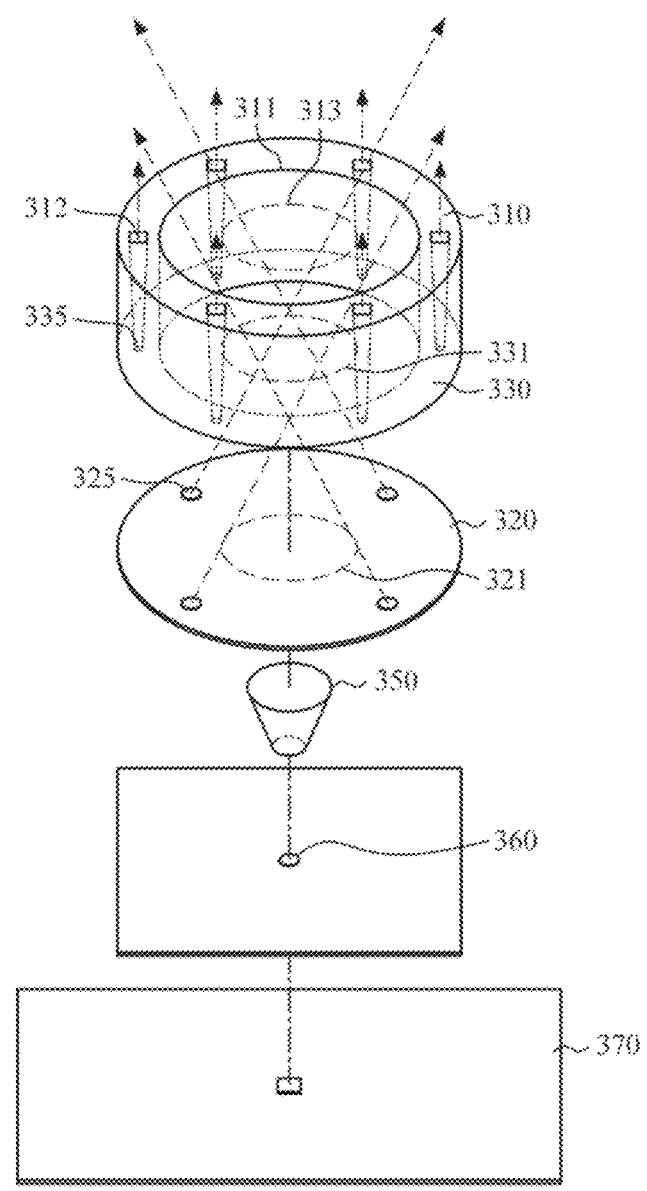
FIGS. 3A, 3B and FIGS. 4A, 4B are diagrams for explaining a structure of a sensor according to an exemplary embodiment.

Referring to FIG. 3A, the sensor 110 may include a cover surface 310 to be in contact with the object, a first substrate 320 disposed on a lower portion of the cover surface 310, and a second substrate 330 disposed between the cover surface 310 and the first substrate 320. A first light emitter 325 may be disposed on the first substrate 320, and a second light emitter 335 may be disposed on the second substrate 330. As illustrated, the second substrate 330 having the second light emitter 335 is disposed thereon may be positioned relatively closer to the cover surface 310 than to the first substrate 320, so that the second light emitter 335 is disposed closer to the cover surface 100 than to the first substrate 320.

The cover surface 310 may include a first transmissive region 311 formed to allow the first light emitted from the first light emitter 325 to be directed toward the object.

The cover surface 310 may include a second transmissive region 312 formed to allow the second light emitted from the second light emitter 335 to travel toward the object. The second transmissive region 312 may have a circular shape as illustrated, but the shape of the second transmissive region 312 is not limited thereto, such that the second transmissive region 312 may be formed in various shapes, such as a rectangular shape, an elliptical shape, or other polygonal shape. In addition, the second transmissive region 312 may be sealed with a cover made of a transparent material, such as glass or plastic, so that light can pass therethrough. In this case, each of a plurality of second transmissive regions 312 may be sealed with an individual cover, or a single unitary cover may be formed to seal all six second transmissive regions 312.

The cover surface 310 may include a third transmissive region 313 that guides the first light and second light scattered or reflected from the subject to be directed toward the light detector.

The remaining region of the cover surface 310 except for the first transmissive region 311, the second transmissive region 312, and the third transmissive region 313 may be a non-transmissive region.

In FIG. 3A, the cover surface 310 is illustrated as a circular shape, which is the same as the second substrate 330, but the present disclosure is not limited thereto, such that the shape of the cover surface 310 may be different from the second substrate 330. For example, a region within a predetermined radius from the center of the cover surface may be horizontal and an outer region beyond the radius may have a cross-section whose height gradually decreases as the distance to the center increases.

The first light emitter 325 is disposed on the first substrate 320. The first light emitted by the first light emitter 325 may pass through the first transmissive region 311 of the cover surface 310 to reach the object. The first light emitter 325 may include a plurality of light sources as illustrated. In FIG. 3A, the first light emitter 325 is illustrated as including four light sources, but the number of light sources is not limited thereto and may vary without limitation.

As described above, the first light emitter 325 may be disposed farther apart from the cover surface than from the second light emitter 335. Therefore, the first light emitted by the first light emitter 325 has a longer optical path than that of the second light emitted by the second light emitter 335. At this time, the first light may be emitted to the object in the form of scattered light.

In addition, the first substrate 320 may include a fourth transmissive region 321 formed to allow the first light and second light scattered or reflected from the object to pass in the direction toward the light detector.

In another example, the first substrate 320 may be omitted. The first light emitter 325 may be disposed on the same surface as the second light emitter 335 of the second substrate 330, and the cover surface 310 may further include a separate transmissive region so that the first light emitter can emit light to the object through the separate transmissive region. The sensor 110 may further include a prism disposed on the optical path of the first light, and a scattering part including an optical film. The first light emitted from the first light emitter 325 may travel to the object in the form of scattered light through the scattering part.

The second light emitter 335 is disposed on the second substrate 330. The second light emitted by the second light emitter 335 may pass through the second transmissive region 312 of the cover surface 310 to reach the object. The second light emitter 335 may include a plurality of light sources arranged along an outer periphery of a fifth transmissive region 331. In FIG. 3A, the second light emitter 335 is illustrated as including six light sources, but the number of light sources is not limited thereto and may vary without limitation.

The second substrate 330 may include the fifth transmissive region 331 at the center so that the first light emitted from the first light emitter 325 passes in the direction toward the object. In addition, the first light and second light scattered or reflected from the object may be guided toward a light detector 360 through the fifth transmissive region 331.

Referring to FIG. 3A, the third transmissive region 313 of the cover surface 310 described above, the fourth transmissive region 321 of the first substrate 320, and the fifth transmissive region 331 of the second substrate 330 are all illustrated as circular shapes of the same size. However, the present disclosure is not limited thereto, such that the third transmissive region 313, the fourth transmissive region 321, and the fifth transmissive region 331 may each have a different size and/or shape from one another.

The sensor 110 may further include a condenser 350 that condenses the first light and the second light scattered or reflected from the object in the direction toward the light detector 360. The condenser 350 may be disposed between the first substrate 320 and the light detector 360 as illustrated.

The light detector 360 may be disposed below the condenser 350 as illustrated. The light detector 360 may include a photodiode, a photo transistor (PTr), an image sensor, for example, a CMOS image sensor or a CCD image sensor.

A force sensor 370 may be disposed below the light detector 360. However, the present disclosure is not limited thereto, such that the force sensor 370 may be disposed between the cover surface 310 and the second substrate 330, or between the first substrate 320 and the second substrate 330.

Figure 3B:
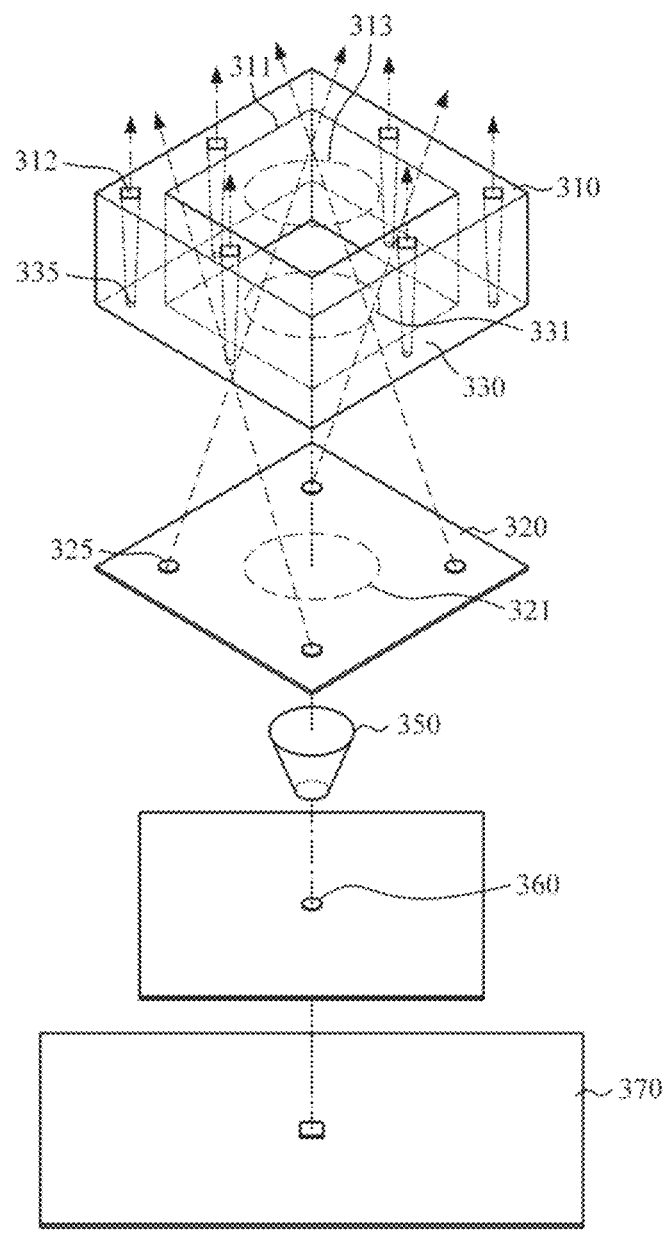

Referring to FIG. 3B, unlike FIG. 3A, the cover surface 310, the first substrate 320, and the second substrate 330 are illustrated as rectangular shapes, rather than circular shapes. The shapes of the cover surface 310, the first substrate 320, and the second substrate 330 are not limited thereto, and they may be formed in various shapes, such as a triangle, a pentagon, and the like.

In addition, unlike FIG. 3A and FIG. 3B, the cover surface 310, the first substrate 320, and the second substrate 330 may each have a different shape and size from one another. For example, the second substrate 330 may be formed in a rectangular shape and the cover surface may be formed in a circular shape.

Figure 4A:
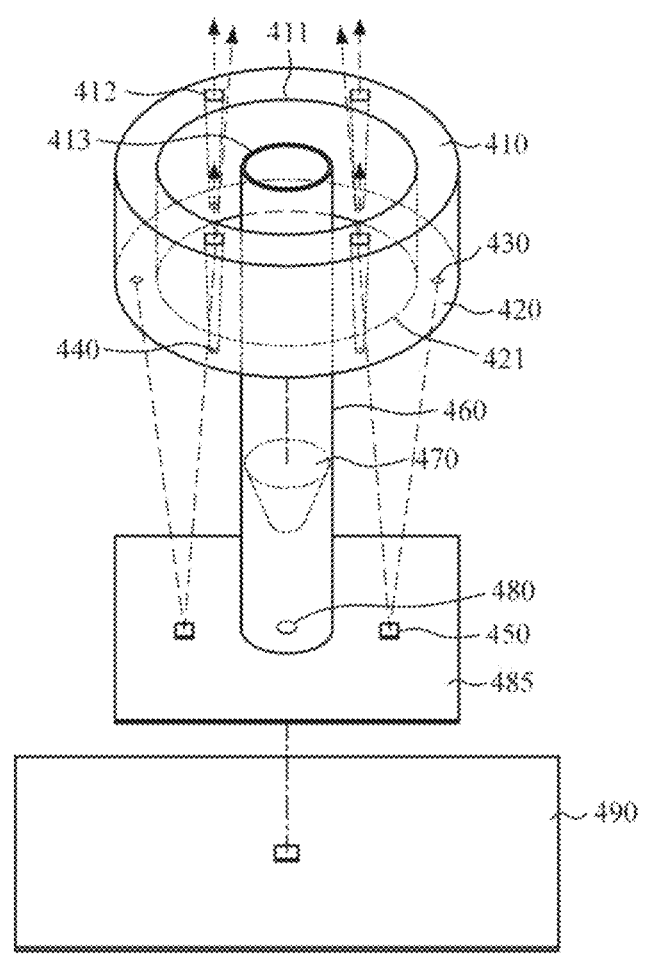

FIG. 4A is a diagram for explaining the structure of the sensor 110 of FIG. 1 according to another exemplary embodiment. Referring to FIG. 4A, the sensor 110 may include a cover surface 410 to be in contact with an object, a substrate 420 disposed below the cover surface 410, a first light emitter 430 disposed on one surface of the substrate 420, for example, a surface opposing the cover surface 410, and configured to emit first light to a reflector 450, a second light emitter 440 disposed on the other surface of the substrate 420, for example, a surface facing toward the cover surface 410, and configured to emit second light to the object, and the reflector 450 configured to reflect the first light emitted from the first light emitter 430 in the direction toward the object. In this case, the reflector 450 may disposed in a direction opposite to the cover surface 410 with respect to the substrate 420.

The sensor 110 may further include a partition wall 460 that blocks the first light emitted from the first light emitter 430 from being directed directly to the light detector 480. In FIG. 4A, the partition wall 460 is illustrated as having a cylindrical shape that extends from a support surface 485 on which the light detector 480 is disposed up to the cover surface 410, but the present disclosure is not limited thereto, such that the partition wall 460 may be formed in a polygonal shape including a triangle and a rectangle.

The cover surface 410 may include a first transmissive region 411 formed to allow the first light, which is emitted from the first light emitter 430 disposed on the substrate 420 and is scattered from the reflector 450, to be directed toward the object.

The cover surface 410 may include a second transmissive region 412 formed to allow the second light emitted from the second light emitter 440 to travel toward the object. The second transmissive region 412 may have a rectangular shape as illustrated, but the shape of the second transmissive region 412 is not limited thereto, such that the second transmissive region 412 may be formed in various shapes, such as polygonal shapes excluding a circular shape, an elliptical shape, and a rectangular shape. In addition, the second transmissive region 412 may be sealed with a cover made of a transparent material, such as glass or plastic, so that light can pass therethrough. In this case, each of a plurality of second transmissive regions 412 may be sealed with an individual cover, or a single unitary cover may be formed to seal all four second transmissive regions 412.

The cover surface 410 may include a third transmissive region 413 that guides the first light and second light scattered or reflected from the subject to be directed toward the light detector 480. The third transmissive region 413 may refer to a space surrounded by the partition wall 460 as illustrated.

The substrate 420 may be disposed below the cover surface 410, and the first light emitter 430 and the second light emitter 440 may be disposed on the substrate 420. At this time, the first light emitter 430 may be disposed on one surface of the substrate 420 and the second light emitter 440 may be disposed on the other surface of the substrate 420.

Figure 4B:
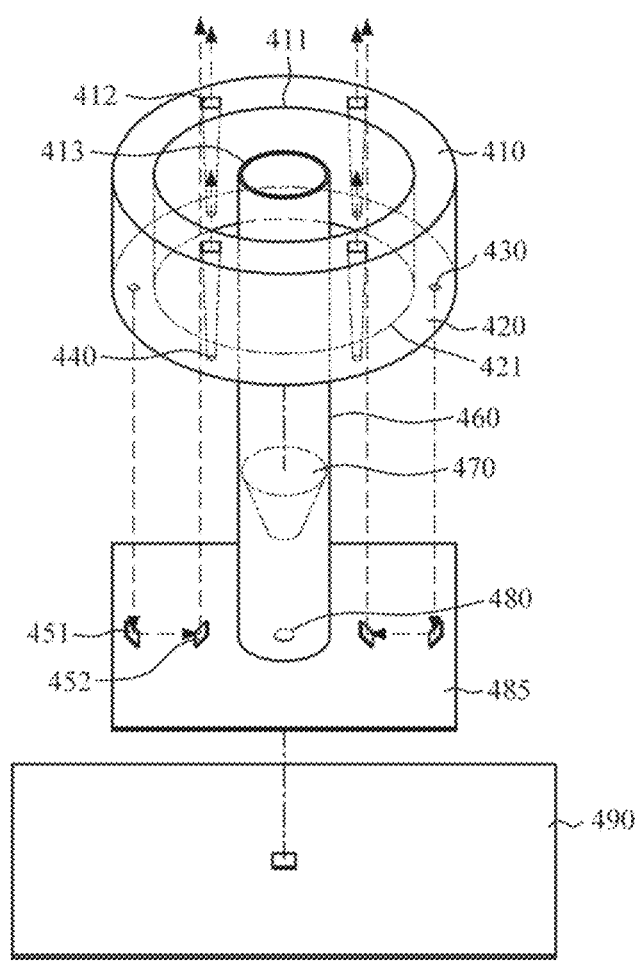

The substrate 420 of FIG. 4A is illustrated as a circular shape, which is the same as the cover surface 410, but the present disclosure is not limited thereto, such that the shape of the substrate 420 may be different from the cover surface 410. In addition, FIG. 4A and FIG. 4B illustrate that the cover surface 410 and the substrate 420 have a circular shape, but the present disclosure is not limited thereto, such that the cover surface 410 and the substrate 420 may be formed in various shapes, such as polygonal shapes including a triangle and a rectangle.

The substrate 420 may include a fourth transmissive region 421 formed to allow the first light reflected from the reflector 450 to be directed toward the object. The partition wall 460 may pass through the center of the fourth transmissive region 421. In this case, the first light and the second light scattered or reflected from the object may be directed toward the light detector 480 through the inner space of the partition wall in the transmissive region.

As illustrated, the first light emitter 430 may be disposed on one surface of the substrate 420 and emit the first light to the reflector 450. In this case, the one surface of the substrate may be a surface in a direction opposite to the cover surface 410, that is, a surface farther away from the cover surface 410. As illustrated, the first light emitter 430 may include a plurality of light sources. In FIG. 4A, the first light emitter 430 includes two light sources, but the number of light sources is not limited thereto and may vary without limitation.

The reflector 450 may be disposed on a support surface 485 in a direction opposite to the cover surface with respect to the substrate 420, and may reflect the first light emitted from the first light emitter 430 toward the object. The reflector 450 may reflect the first light emitted from the first light emitter 430 toward the fourth transmissive region 421 of the substrate 420 so that the first light can be emitted in the direction toward the object. Therefore, the first light emitted by the first light emitter 430 has a longer optical path than that of the second light emitted by the second light emitter 440, and may thus be emitted to the object in the form of scattered light.

The second light emitter 440 may be disposed on the other surface of the substrate 420 and emit the second light to the object. In this case, the other surface of the substrate 420 may be a surface positioned in the direction of the cover surface 410, that is, a surface closer to the cover surface 410. As illustrated, the second light emitter 440 may include a plurality of light sources. In FIG. 4A, the second light emitter 440 includes four light sources, but the number of light sources is not limited thereto and may vary without limitation.

The sensor may further include a condenser 470 that condenses the first light and second light scattered or reflected from the subject in the direction toward the light detector 480.

The sensor may include the light detector 480 configured to detect a first light signal scattered or reflected from the object based on the first light and detect a second light signal scattered or reflected from the object based on the second light, and may further include a force sensor 490 configured to measure a force applied to the object when the object is in contact with the cover surface 410.

As illustrated, the light detector 480 may be disposed on the support surface 485 positioned below the condenser 470. The light detector 480 may include a photodiode, a photo transistor (PTr), an image sensor, for example, a CMOS image sensor or a CCD image sensor.

In FIG. 4A, the reflector 450 and the light detector 480 are illustrated as being disposed on the same support surface 485, but the reflector 450 may be disposed on a distinct support surface different from a support surface on which the light detector 480 is disposed. For example, the support surface on which the reflector 450 is disposed may be closer to the cover surface than to the support surface on which the light detector 480 is disposed.

The force sensor 490 may be disposed below the light detector 480. However, the present disclosure is not limited thereto, such that the force sensor 490 may be disposed between the cover surface 410 and the substrate 420.

Referring to FIG. 4B, unlike FIG. 4A, the sensor may include a first reflector 451 disposed in a direction opposite to the cover surface 410 with respect to the substrate 420 and configured to reflect the first light emitted from the first light emitter 430 toward a second reflector 452, and the second reflector 452 configured to reflect the first light reflected from the first reflector 451 toward the object.

The first reflector 451 may reflect the first light emitted from the first light emitter 430 toward the second reflector 452, and the second reflector 452 may reflect the first light reflected from the first reflector 451 toward the object. The second reflector 452 may reflect the first light reflected from the first reflector 451 toward the fourth transmissive region 421 of the substrate 420 so that the first light can be emitted in the direction toward the object. Therefore, the first light emitted by the first light emitter 430 has a longer optical path than that of the second light emitted by the second light emitter 440, and may thus be emitted to the object in the form of scattered light.

In this case, the first and second reflectors 451 and 452 may be disposed on the support surface 485 in a direction opposite to the cover surface 410 with respect to the substrate 420. In addition, as illustrated in FIG. 4B, the first reflector 451 and the second reflector 452 may be disposed on the same support surface 485 to have parallel heights, but the present disclosure is not limited thereto, such that the first reflector 451 and the second reflector 452 may be disposed on different support surfaces and have different heights.

Referring back to FIG. 1, the processor 120 is included in the apparatus 100 for estimating biological information.

The processor 120 may be connected to the sensor 110 through electrical, mechanical, or wired/wireless communication. The processor 120 may control the first light emitter, the second light emitter, and the force sensor. For example, when a request for estimating biological information is received according to a user's manipulation, and the object is in contact with the cover surface of the sensor 110, the processor 120 may control the intensity of light, duration of light, and on/off of the first light emitter. In addition, the processor 120 may control power supply to the force sensor.

The processor 120 may receive measured data from the first light emitter, the second light emitter, and the force sensor, and process the received data. Upon receiving the first light signal and the second light signal from the sensor 110, the processor 120 may perform preprocessing on the first light signal and the second light signal, such as filtering for removing noise, amplification of the first light signal and the second light signal, or conversion into digital signals. For example, the processor 120 may perform bandpass filtering on the second light signal received from the sensor 110, using a bandpass filter having a preset passband (e.g., a passband from 0.4 Hz to 10 Hz) to remove noise from the second light signal. Also, the processor 120 may perform correction through fast Fourier transform-based reconstruction of the second light signal. However, the present disclosure is not limited thereto, and various types of preprocessing may be performed according to various measurement environments, such as the computing performance or measurement accuracy of the apparatus, the purpose of biological information estimation, the measurement part of the user, the temperature of the object, humidity, the temperature of the sensor, and the like.

The processor 120 may estimate biological information based on the first light signal and the second light signal detected by the sensor 110. At this time, the biological information may include at least one of heart rate, oxygen saturation, respiration rate, triglycerides, blood pressure, arterial stiffness, skin age, vascular age, blood sugar, electrolytes, carotenoids, body moisture, protein, alcohol, and an antioxidant index. However, the features are not limited thereto.

As described with reference to FIGS. 3A to 4B, since the first light emitter is farther apart from the cover surface than from the second light emitter or the first light is reflected by the reflector, the first light has a longer optical path than that of the second light, and accordingly, the first light is emitted to the object in the form of scattered light. In this case, the processor 120 may determine whether a condition is satisfied based on the first light signal detected by the sensor 110 and may estimate biological information based on the second light signal.

The processor 120 may determine whether the condition is satisfied based on at least one of the first light signal detected by the sensor 110 or the measured force. For example, the processor 120 may obtain a contact image of the object based on the first light signal and determine the contact state of the object based on at least one of the obtained contact image or the measured force. In particular, the processor 120 may determine whether the condition is satisfied based on the determined contact state.

For example, the processor 120 may obtain the contact image based on the intensity of the received first light signal, image data, fingerprint data, and the like, and determine the contact state including at least one of whether the object is in contact or a contact position based on the obtained contact image. For example, the processor 120 may extract a characteristic point, for example, a central point of a fingerprint, from the obtained contact image, and determine whether the contact state is normal by detecting whether the extracted characteristic point is outside a predetermined range.

In another example, the contact state of the object may be determined based on whether a value of the measured contact force exceeds or falls below a threshold value, the measurement time of the contact force, whether a contact force exceeding a predefined threshold is measured for a threshold period or longer, or the like. For example, it may be determined that the contact state of the object is normal when at least one of the following conditions is satisfied: a value of the measured contact force is within a threshold range, the force is measured for a threshold period or longer, or the force gradually increases with time. Such conditions for determination may be predefined in various ways.

The processor 120 may determine whether the condition for estimating biological information is satisfied based on the determined contact state. For example, when the central point of the fingerprint extracted from the obtained contact image does not exceed a predetermined range and a value of a contact force is measured for a threshold period within a threshold range, the processor 120 may determine that the condition for estimating biological information is satisfied.

When it is determined that the condition for estimating biological information is not satisfied based on the determined contact state, the processor 120 may guide the user to adjust the contact state.

For example, when it is determined that the condition for estimating biological information is not satisfied based on the obtained contact image, the processor 120 may present, on a display, a graphical object representing, for example, a finger, to induce normal contact of the object, for example, a fingertip, with the cover surface, together with a graphical object representing the cover surface. In this case, a text object for inducing a normal contact of the object with the cover surface may be included.

Figure 5A:
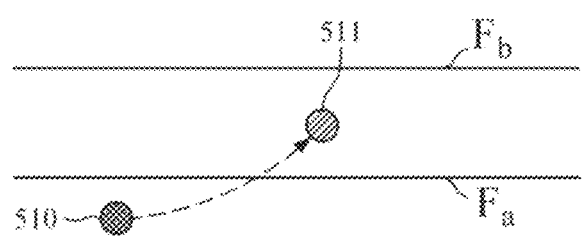
FIGS. 5A and 5B are diagrams illustrating an example of a screen in which a guide graph is output to a user to adjust a contact state.
Figure 5B:
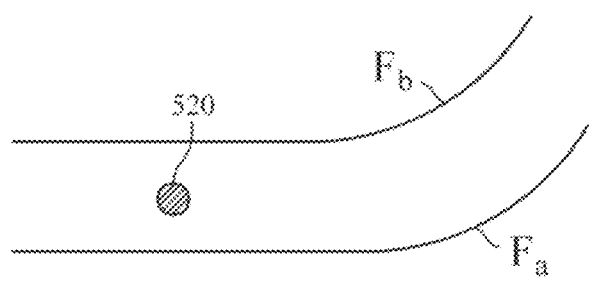

In another example, when it is determined that the condition for estimating biological information is not satisfied based on the measured force, the processor 120 may guide the user to adjust the contact state by providing guide information on the contact force to the user. A process of providing guide information on a contact force to the user is described with reference to FIGS. 5A and 5B. FIGS. 5A and 5B are diagrams illustrating an example of a screen in which a guide graph is output to a user to adjust a contact state.

For example, FIG. 5A illustrates a screen in an initial state of measurement in which an initial contact force is adjusted with a finger, and FIG. 5B illustrates a screen after the initial contact force falls within a normal range.

Referring to FIG. 5A, the processor 120 may present graphical objects $F_a$ and $F_b$ representing predefined reference contact forces and graphical objects 510 and 511 representing actual contact forces received from the force sensor on a display.

For example, as illustrated, the lower limit $F_a$ and the upper limit $F_b$ of the graphical objects representing the reference contact forces may include lines, continuous points, circles, ellipses, polygons, and the like. Similarly, the graphical objects 510 and 511 representing the actual contact forces may include circles, ellipses, polygons, crosses, arrows, and the like.

Referring to FIG. 5A, the processor 120 may present the lower limit $F_a$ and the upper limit $F_b$ of the graphical objects representing the reference contact forces in the horizontal direction on the display screen at the initial stage of the measurement. In addition, when the initial contact force received from the force sensor is outside the lower limit $F_a$ and the upper limit $F_b$, for example, when the initial contact force is less than the lower limit $F_a$ of the reference contact force, or when the initial contact force is not measured, the graphical object 510 for the actual contact force may be displayed under the lower limit object $F_a$.

In addition, when the actual contact force enters the normal range as the user adjusts the force pressing the sensor with his/her finger, the graphical object 511 for the actual contact force may be displayed at a position between the upper limit object $F_a$ and the lower limit object $F_b$, corresponding to the actual contact force. In this case, the graphical object 510 for the actual contact force may be displayed as if it moves along the trajectory from an initial position (corresponding to the position of the graphical object 510) to a final position (corresponding to the position of the graphical object 511) so that the change in the actual contact force can be shown. In an embodiment, the trajectory from the initial position to a current position may be displayed on the display screen while continuously updating the location of the graphic object 510 according to the change in the actual contact force.

In addition, the graphical object for the actual contact force outside the normal range and the graphical object 511 for the actual contact force within the normal range may be distinguished from each other by different shapes or colors, thereby allowing the user to easily recognize them.

Referring to FIG. 5B, when the actual contact force falls within the normal range at the initial stage of the measurement, the processor 120 may change the graphical objects $F_a$ and $F_b$ representing the reference contact forces that are horizontally arranged as shown in FIG. 5A to a shape that gradually bends upwards so that the user can gradually increase the pressing force of the finger with time. In this way, the graphical objects $F_a$ and $F_b$ representing the reference contact forces may be changed to an upward or downward direction according to the change of the reference contact forces during the period of measurement of biological information.

When it is determined that the condition for estimating biological information is satisfied based on the received first light signal and/or the contact force, the processor 120 may turn off the first light emitter and turn on the second light emitter.

When the second light signal is received through the sensor 110, the processor 120 may estimate biological information based on the received second light signal.

The processor 120 may further determine whether a condition for estimating biological information is satisfied based on the received second light signal, and may estimate biological information based on the determination result. In this case, the processor 120 may determine whether the condition for estimating biological information is satisfied based on the light intensity or a signal to noise ratio (SNR) of the received second light signal. For example, the processor 120 may calculate an SNR of the received second light signal, and may determine that the condition is satisfied only when the calculated SNR exceeds an allowable threshold.

When it is determined that the condition for estimating the biological information is not satisfied, the processor 120 may re-obtain the second light signal by driving the second light emitter.

When it is determined that the condition is satisfied, the processor 120 may estimate biological information using the second light signal. For example, features may be extracted from the received second light signal, and the extracted features may be applied to a predetermined biological information estimation model to estimate biological information. In particular, the features may include an amplitude value, force/pressure, and time at the maximum or minimum point of the second light signal, times and amplitudes corresponding to the local minimum point/local maximum point of the first and second differential signal waveforms of the second light signal, the partial or entire area of the second light signal waveform, or the combinations thereof. However, the features are not limited thereto. The biological information estimation model may be defined as various linear or non-linear combination functions, such as addition, subtraction, division, multiplication, logarithmic value, regression equation, and the like, with no specific limitation.

In another example, the processor 120 may obtain an oscillometric envelope based on the received second light signal and the measured force and acquire the feature from the obtained oscillometric envelope. For example, an amplitude value at a maximum peak point in the oscillometric envelope, a contact pressure value at the maximum peak point, contact pressure values at the right and left points, which are symmetrically distant from the contact pressure value at the maximum peak point and which have a preset peak ratio within a range from 0.5 to 0.7 may be obtained as the features for blood pressure estimation. Upon obtaining the features, the processor 120 may estimate blood pressure by applying a predefined blood pressure estimation model to the features.

Figure 5C:
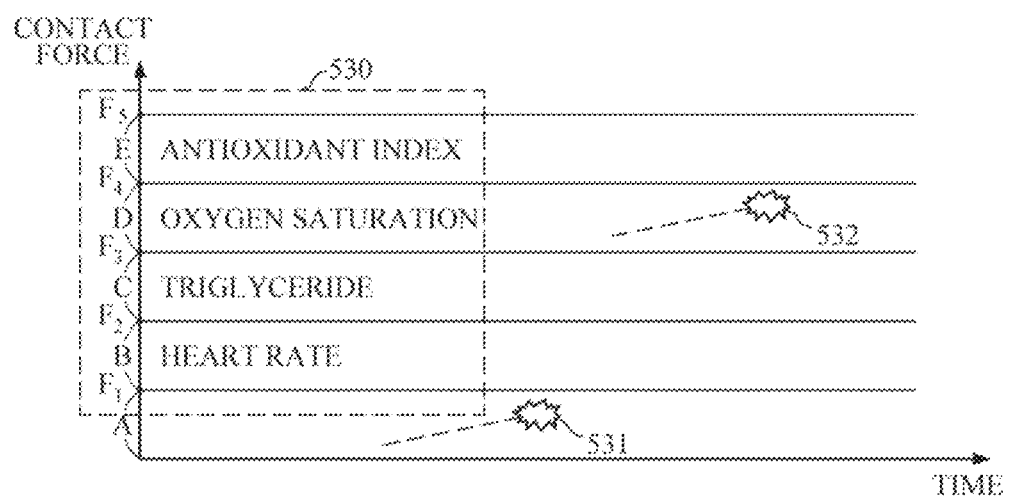
FIG. 5C illustrates a graphical object related to a reference force and a graphical object related to an actual contact force for each of a plurality of biological information.

Meanwhile, the processor 120 may determine biological information to be estimated from among a plurality of biological information based on the contact force measured by the force sensor. A process of determining biological information to be estimated based on the measured contact force is described with reference to FIG. 5C. FIG. 5C illustrates a graphical object related to reference forces (e.g., target forces) for each of a plurality of biological information (e.g., a plurality of different biological information types) and graphical objects 531 and 532 related to the actual contact forces. The storage 210 may store the reference forces that respectively correspond to the plurality of biological information. For example, a first reference force range from $F_1$ to $F_2$, a second reference force range from $F_2$ to $F_3$, a third reference force range from $F_3$ to $F_4$, a fifth reference force range from $F_4$ to $F_5$ may be stored in the storage 210, as target forces for obtaining hear rate information, triglyceride information, oxygen saturation information, and antioxidant index information, respectively.

When a request for estimating biological information is received, the processor 120 may output a graph for guiding reference forces for a plurality of biological information as shown in FIG. 5C before or after determining whether the condition for estimating biological information is satisfied as described above. For example, when the contact state of the object is determined to be normal or meet a preset contact quality based on the obtained contact image, the processor 120 may output the graph as shown in FIG. 5C, and may determine biological information to be estimated from among the plurality of biological information based on the measured contact force.

As illustrated, the processor 120 may display a first graphical object 530 representing the reference forces for each of the plurality of biological information. In addition, when the actual contact force is measured by the force sensor in real time, the processor 120 may present a second graphical object 531 or 532 representing the measured contact force on the display. In this case, the reference force for each of the plurality of biological information may be predefined. The reference force 530 for each biological information may be a fixed value defined for a plurality of users, and may be received in advance from an external device. Alternatively, the reference force 530 for each biological information may be adjusted for each user by the processor 120. For example, the reference force may be calibrated based on user characteristic information, such as a user's health status, age, gender, etc., or existing measurement data, for example, measurement space of each user, measurement time point, user's fingerprint data, the contact area of an object for each user, and the like.

For example, the processor 120 may determine a type of biological information to be estimated, and may identify the reference force to which the actual contact force is supposed to reach for estimating the biological information. In this case, only when the actual contact force is measured in a specific section for a threshold period or longer, or only when the contact force gradually increases over time in a specific section, the biological information in the corresponding section may be determined as the biological information to be estimated.

For example, referring to FIG. 5C, when the actual contact force measured by the force sensor is in section D $F_3$ to $F_4$, the processor 120 may output the graphical object 532 representing the actual contact force on the corresponding section D, and determine oxygen saturation corresponding to section D as the biological information to be estimated. In this case, only when the contact force is measured in section D $F_3$ to $F_4$ for a threshold period or longer, or only when the contact force gradually increases over time in section D $F_3$ to $F_4$, the processor may determine that the biological information to be measured is oxygen saturation.

When the actual contact force measured by the force sensor is not measured in any one of section B $F_1$ to $F_2$, section C $F_2$ to $F_3$, section D $F_3$ to $F_4$, and section E $F_4$ to $F_5$ for a threshold period or longer, or when the contact force does not gradually increase over time in any one of section B $F_1$ to $F_2$, section C $F_2$ to $F_3$, section D $F_3$ to $F_4$, and section E $F_4$ to $F_5$, the processor may determine that the user's motion noise has occurred. In this case, the processor may request the user to re-measure biological information or may guide the user to gradually increase force within a range of any one of sections B, C, D, and E for longer than the threshold period.

As another example, when the actual contact force measured by the force sensor is in section A0 to $F_1$, a second graphical object 531 representing the actual contact force may be displayed on section A, and at this time, since biological information that can be estimated is not present, the user may be guided to increase the contact force.

Figure 5D:
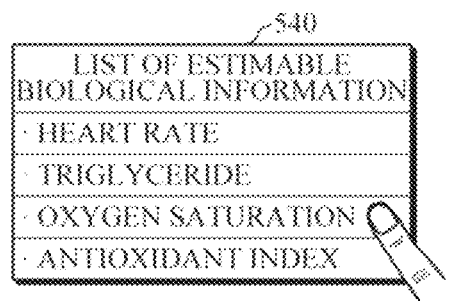
FIG. 5D is a diagram illustrating a list of a plurality of biological information provided to a user.
Figure 5E:
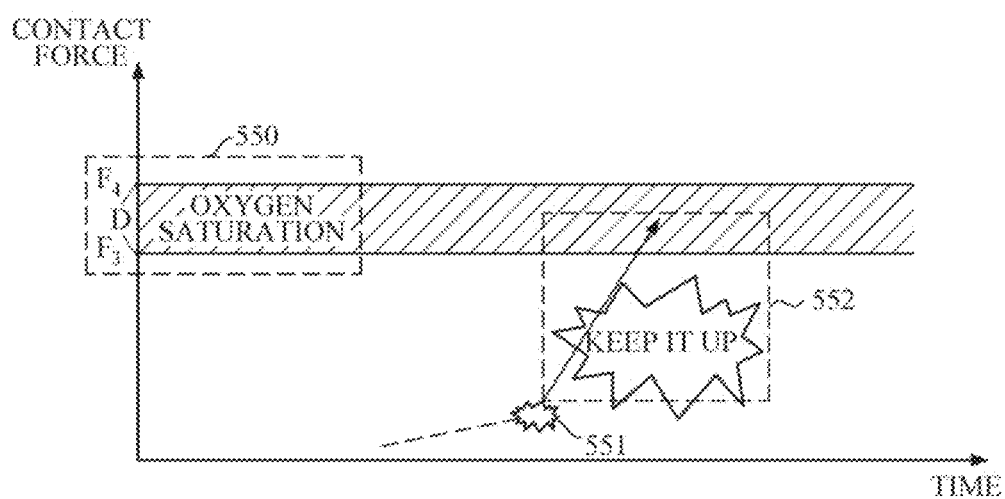
FIG. 5E illustrates a graphical object related to a reference force for biological information selected by a user, and a graphical object related to an actual contact force.

FIG. 5D is a diagram illustrating a list of a plurality of biological information provided to a user. FIG. 5E illustrates a graphical object related to a reference force for biological information selected by a user, and a graphical object related to an actual contact force.

Referring to FIGS. 1, 5D, and 5E, the processor 120 may provide a list of a plurality of biological information (e.g., a list of a plurality of different bio-information types) to the user, and determine that the biological information selected by the user is biological information to be estimated.

For example, upon receiving a request for estimating biological information, the processor 120 may output a list 540 of estimable biological information as shown in FIG. 5D to the display.

When the user selects oxygen saturation from the biological information list 540 output to the display, the processor 120 may determine that the oxygen saturation selected by the user is the biological information to be estimated, and may output a graph of oxygen saturation as shown in FIG. 5E. In this case, the reference force of each of the plurality of biological information may be defined in advance, and it has been described in detail with reference to FIG. 5C, and is thus omitted herein.

As illustrated, the processor 120 displays a graphical object 550 representing a reference force for the oxygen saturation selected by the user on the output graph, and when an actual contact force is measured by the force sensor, the processor 120 may output a graphical object 551 representing the measured actual contact force.

Referring to FIG. 5E, it can be seen that the user's actual contact force is smaller than the reference force (section D, $F_3$ to $F_4$) for the oxygen saturation, which is the biological information selected by the user. The processor may guide the user to apply a force corresponding to the reference force of the biological information to be estimated. For example, as illustrated, an arrow for guiding the user to move a position of the actual contact force to a position of the reference force, or a text graphical object 552, such as "keep it up" "put more strength," or "press harder" for encouraging the user to further apply force may be output. Alternatively, a graphical object 551 representing the actual contact force may be displayed in a unique shape (e.g., star shape, triangle, etc.) or may be displayed using a color (e.g., red) that can be easily recognized by the user, the thickness of a line, and the like. In another example, the actual contact force of the user and the reference force of oxygen saturation may be numerically displayed to indicate how much force the user should apply more.

The processor 120 may control at least one of the wavelength, current intensity, and duration of the second light emitter according to the biological information to be estimated that is determined based on the measured contact force or the driving condition of the second light emitter corresponding to the biological information selected by the user.

Figure 2:
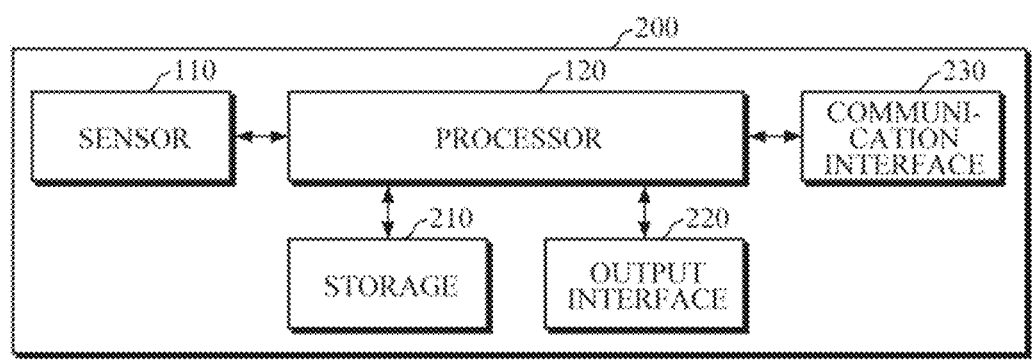
FIG. 2 is a block diagram illustrating an apparatus for estimating biological information according to another exemplary embodiment.

FIG. 2 is a block diagram illustrating an apparatus for estimating biological information according to another exemplary embodiment.

Referring to FIG. 2, an apparatus 200 for estimating biological information may include a processor 120, a storage 210, an output interface 220, and a communication interface 230. The sensor 110 and the processor 120 are described in detail with reference to FIGS. 1, 3A to 4B, 5A, and 5B, and thus hereinafter, description will be given of configurations that are not redundant.

The storage 210 may store reference information for biological information estimation, and processing results of the sensor 110 and/or the processor 120. In this case, the reference information may include user information such as a user's age, gender, and health status, a normal contact state, such as a contact position of a finger, a driving condition of a light source, a reference contact force, or a biological information estimation model. However, the reference information is not limited thereto.

In this case, the storage 210 may include at least one type of storage medium, such as a flash memory type, a hard disk type, a multimedia card micro type, a card type memory (e.g., SD or XD memory) random access memory (RAM), static random access memory (SRAM), read-only memory (ROM), electrically erasable programmable read-only memory (EEPROM), programmable read-only memory (PROM), a magnetic memory, a magnetic disk, and an optical disk, but is not limited thereto.

The output interface 220 may display graphical objects related to the contact state, including the contact position, and a contact force through a display. In addition, when an estimated biological information value is obtained, the output interface 220 may visually display the estimated biological information value through the display. In this case, when the result of biological information estimation falls outside a normal range, alarm/warning information may be visually output. Alternatively, warning information on the contact state, contact force, and estimated biological information value may be output using a non-visual output means, such as a voice or haptic device.

The communication interface 230 may communicate with an external device under the control of the processor 120 to transmit and receive various data related to biological information estimation. For example, the communication interface 230 may transmit the processing result of the processor 120 to an external device, and allow the external device to manage the biological information history for the user, monitor the user's health status, output the biological information history and the monitoring result of the health status, and the like. In this case, the external device includes a smartphone, a tablet PC, a desktop PC, a notebook PC, and the like, and may include a device used in a medical institution including a cuff-type blood pressure measuring device, but is not limited thereto.

In another example, the communication interface 230 may receive a biological information estimation model required for biological information estimation, user characteristic information, and the like from the external device. The received information may be stored in the storage 210.

In this case, the communication interface 230 may communicate with the external device by using Bluetooth communication, Bluetooth low energy (BLE) communication, near field communication (NFC), wireless local access network (WLAN) communication, ZigBee communication, infrared data association (IrDA) communication, Wi-Fi Direct (WFD) communication, ultra-wideband (UWB) communication, Ant+ communication, Wi-Fi communication, radio frequency identification (RFID) communication, 3G communication, 4G communication, and/or 5G communication. However, these are merely examples, and the embodiment is not limited thereto.

FIG. 6 is a flowchart illustrating a method of estimating biological information according to an exemplary embodiment. The method of FIG. 6 may be one exemplary embodiment of a biological information estimating method performed by the apparatuses 100 and 200 for estimating biological information of FIGS. 1 and 2. Hereinafter, the method will be described in brief to avoid redundancy.

First, a first light signal is detected by emitting first light to an object in operation 610, and a force between the object and the cover surface of a sensor may be measured in operation 620.

Then, whether a condition for estimating biological information is satisfied may be determined based on the detected first light signal and the measured force in operation 630. In particular, a contact image of the object may be obtained based on the detected first light signal, and a contact state of the object may be determined based on at least one of the obtained contact image or the force measured by the force sensor. Whether the condition for estimating biological information is satisfied may be determined based on the determined contact state.

When it is determined in operation 640 that the condition for estimating biological information is not satisfied, the first light signal is re-detected by emitting first light to the object in operation 610, and the force between the object and the cover surface may be measured again in operation 620.

When it is determined in operation 640 that the condition for estimating biological information is satisfied, a second light signal may be detected by emitting second light to the object through the second light emitter in operation 650.

Thereafter, whether a condition for estimating biological information is satisfied may be determined based on the detected second light signal in operation 660. At this time, whether the condition for estimating biological information is satisfied may be determined based on an SNR of the detected second light signal.

When it is determined in operation 670 that the condition for estimating biological information is not satisfied, the second light signal may be re-detected by emitting the second light to the object through the second light emitter in operation 650.

When it is determined in operation 670 that the condition for estimating biological information is satisfied, biological information may be estimated in operation 680.

Figure 7A:
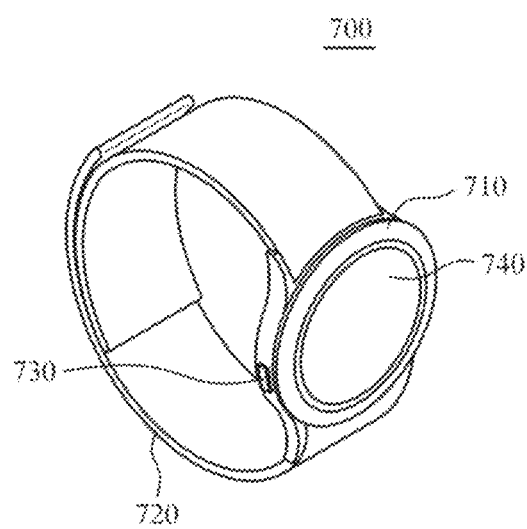
FIG. 7A is a diagram illustrating an electronic device according to an exemplary embodiment.

FIG. 7A illustrates an electronic device according to an exemplary embodiment. An electronic device 700 according to embodiments may be a smart watch or a smart band-type wearable device. However, the implementation of the electronic device 700 is not limited thereto, and may be a mobile device, such as a smartphone or a tablet PC.

Referring to FIG. 7A, the electronic device 700 may include a main boy 710 and a strap 720.

The main body 710 may include modules for performing general functions of the electronic device 700 and a sensor 730 for estimating biological information A battery may be embedded in the main body 710 or the strap 720 to supply power to various modules. The strap 720 may be connected to the main body 710. The strap 720 may be flexible so as to be bent around a user's wrist. The strap 720 may include a first strap and a second strap that is separated from the first strap. One ends of the first strap and the second strap may be connected to each end of the main body 710 and the first strap and the second strap may be fastened to each other using fastening means formed on the other sides thereof. In this case, the fastening means may be formed as Velcro fastening, pin fastening, or the like, but is not limited thereto. In addition, the strap 720 may be formed as one integrated piece, such as a band, which is not separated into pieces.

A display 740 may be disposed on a top surface of the main body 710 to visually display various types of information. The display 740 may include a touch screen panel capable of receiving a touch input of a user.

The sensor 730 may have the structure and functions of the sensor described with reference to FIGS. 1 to 4B, and may be disposed in the form of a button on a side of the main body 710. The sensor 730 may detect the first light signal and the second light signal from an object of the user as described above, and when the object is in contact with the sensor 730, the sensor 730 may obtain information on force applied by the object. Also, the sensor 730 may perform a user interface function for controlling general functions of the electronic device 700, for example, selection/execution of an application, adjustment of a graphical user interface (GUI) of the display 740, and the like.

Figure 7B:
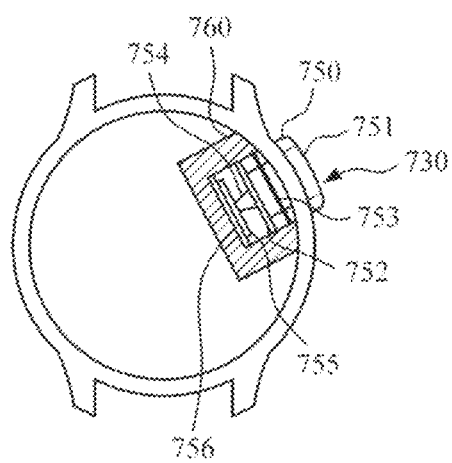
FIG. 7B is a diagram illustrating a structure of a sensor embedded in an electronic device.

FIG. 7B is a diagram for explaining the structure of the sensor 730 embedded in the electronic device.

Referring to FIG. 7B, the sensor 730 may include a housing 750. Also, the sensor 730 may include a first light emitter 752, a second light emitter 753, a condenser 754, a light detector 755, and a force sensor 756, which are disposed inside or in a lower portion of the housing 750.

A portion of the housing 750 may be exposed to the outside through the side of the main body 710 in the form of a button. The housing 750 may include a cover surface 751 which is to be in contact with a finger placed thereon. For example, a supporter 760 inside the main body 710 may support the housing 750 on at least one of the periphery or the lower portion of the housing 750. In an example embodiment of FIG. 7B, the supporter 760 is illustrated as surrounding the housing 750 inside the main body 710, but this is merely an example. Although not illustrated in FIG. 7B, an additional structure for preventing the housing 750 from being dislodged from the main body 710 may be further included in the housing 750 or inside the main body 710.

While not restricted thereto, an example embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an example embodiment may be written as a computer program transmitted over a computer-readable transmission medium, such as a carrier wave, and received and implemented in general-use or special-purpose digital computers that execute the programs. Moreover, it is understood that in example embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. An apparatus for estimating biological information, comprising:
   a sensor configured to detect a first light signal and a second light signal that are reflected or scattered from a body part of a user; and
   a processor configured to determine whether a condition for estimating the biological information is satisfied based on the first light signal, and in response to the biological information being satisfied, estimate the biological information based on the second light signal,
   wherein the sensor comprises:
      a cover surface configured to be in contact with the body part;
      a first light emitter disposed on a first substrate and configured to emit a first light to the body part;
      a second light emitter disposed on a second substrate and configured to emit a second light, the second substrate being disposed closer to the cover surface than to the first substrate;
      a light detector configured to detect the first light signal from the first light that is emitted to and then scattered or reflected from the body part, and detect the second light signal from the second light that is emitted to and then scattered or reflected from the body part; and
      a force sensor configured to measure a force applied to the body part when the body part is in contact with the cover surface, and
   wherein the processor is further configured to provide a list of a plurality of different types of biological information to the user and control the second light emitter according to a driving condition of the second light emitter corresponding to a biological information type selected by the user from the list.

2. The apparatus of claim 1, wherein the processor is further configured to obtain a contact image of the body part based on the first light signal, determine a contact state of the body part based on at least one of the contact image and the force measured by the force sensor, and determine whether the condition for estimating biological information is satisfied based on the determined contact state.

3. The apparatus of claim 2, wherein based on the condition being determined to be not satisfied, the processor is further configured to guide the user to adjust the contact state.

4. The apparatus of claim 2, wherein the processor is further configured to drive the first light emitter when the body part is in contact with the cover surface, and turn off the first light emitter and turn on the second light emitter when the contact state meets a condition for biological information estimation.

5. The apparatus of claim 1, wherein when the second light signal is received by the light detector, the processor is further configured to determine whether the condition for estimating the biological information is satisfied based on a signal to noise ratio (SNR) of the received second light signal.

6. The apparatus of claim 5, wherein based on the condition being determined to be not satisfied, the processor is further configured to drive the second light emitter to re-obtain the second light signal.

7. The apparatus of claim 1, wherein when the body part is in contact with the cover surface and the force is measured by the force sensor, the processor is further configured to determine a type of the biological information to be estimated based on the measured force.

8. The apparatus of claim 7, wherein the processor is further configured to control at least one of a wavelength, current intensity, or duration of the second light emitter according to the driving condition of the second light emitter corresponding to the determined type of the biological information.

9. The apparatus of claim 7, further comprising a display configured to display a first graphical object representing a reference force for each of a plurality of different types of biological information and a second graphical object representing the force measured by the force sensor.

10. The apparatus of claim 1, further comprising a display configured to display a first graphical object representing the plurality of different types of biological information and a second graphical object representing a reference force for the selected biological information type.

11. The apparatus of claim 1, wherein the biological information is at least one of heart rate, oxygen saturation, respiration rate, triglyceride, blood pressure, or antioxidant index.

12. A sensor for measuring a multi-signal, the sensor comprising:
   a cover surface configured to be in contact with an object;
   a first light emitter disposed on a first substrate and configured to emit first light to the object;
   a second light emitter disposed on a second substrate and configured to emit second light to the object;
   the second substrate being disposed closer to the cover surface than to the first substrate;
   a light detector configured to detect a first light signal from the first light that is emitted to and then scattered or reflected from the object, and detect a second light signal from the second light that is emitted to and then scattered or reflected from the object based on the second light; and
   a force sensor configured to measure a force applied to the object when the object is in contact with the cover surface,
   wherein the second substrate comprises a transmissive region at a center of the second substrate to guide the first light and the second light scattered or reflected from the object to be directed toward the light detector, and the second light emitter comprises a plurality of light sources arranged along an outer periphery of the transmissive region.

13. The sensor of claim 12, wherein the first light and the second light have different wavelengths.

14. The sensor of claim 12, further comprising a condenser configured to condense the first light and the second light scattered or reflected from the object in a direction toward the light detector.

* * * * *